(12) United States Patent
Bergemann et al.

(10) Patent No.: US 9,849,076 B2
(45) Date of Patent: Dec. 26, 2017

(54) SHINE-PRODUCING HAIR TREATMENT AGENT

(71) Applicant: Henkel AG & Co. KGaA, Dusseldorf (DE)

(72) Inventors: Uwe Bergemann, Hamburg (DE); Burkhard Mueller, Duesseldorf (DE); Pamela Kaftan, Hamburg (DE)

(73) Assignee: Henkek AG & Co. KGaA, Dusseldorf (DE)

( * ) Notice: Subject to any disclaimer, the term of this patent is extended or adjusted under 35 U.S.C. 154(b) by 392 days.

(21) Appl. No.: 14/360,902

(22) PCT Filed: Oct. 23, 2012

(86) PCT No.: PCT/EP2012/070921
§ 371 (c)(1),
(2) Date: May 27, 2014

(87) PCT Pub. No.: WO2013/079259
PCT Pub. Date: Jun. 6, 2013

(65) Prior Publication Data
US 2015/0030554 A1  Jan. 29, 2015

(30) Foreign Application Priority Data
Nov. 28, 2011 (DE) .................. 10 2011 087 233

(51) Int. Cl.
*A61Q 5/12* (2006.01)
*A61K 8/891* (2006.01)
*A61K 8/37* (2006.01)
*A61K 8/31* (2006.01)
*A61Q 5/00* (2006.01)
*A61K 8/04* (2006.01)

(52) U.S. Cl.
CPC .............. *A61K 8/891* (2013.01); *A61K 8/046* (2013.01); *A61K 8/31* (2013.01); *A61K 8/37* (2013.01); *A61Q 5/00* (2013.01); *A61Q 5/12* (2013.01); *A61K 2800/59* (2013.01)

(58) Field of Classification Search
CPC . A61K 8/34; A61K 8/362; A61K 8/49; A61K 8/4946; A61K 8/4973; A61K 8/498; A61Q 19/00; A61Q 5/06; A61Q 5/12; A61Q 1/06; A61Q 1/10; A61Q 5/65
See application file for complete search history.

(56) References Cited

U.S. PATENT DOCUMENTS

| | | | |
|---|---|---|---|
| 6,432,912 B1* | 8/2002 | Rodelet | A61K 8/375 424/76.4 |
| 9,242,923 B2* | 1/2016 | St. Laurent | A61K 9/00 |
| 2007/0166254 A1 | 7/2007 | Bianchi | |
| 2009/0214455 A1* | 8/2009 | Blin | A61K 8/19 424/63 |
| 2010/0215785 A1 | 8/2010 | Kizoulis et al. | |
| 2010/0310644 A1* | 12/2010 | Liebmann | A61K 8/64 424/450 |
| 2012/0237464 A1* | 9/2012 | Ahn | A61K 8/89 424/59 |

FOREIGN PATENT DOCUMENTS

| | | | | |
|---|---|---|---|---|
| DE | 102007063352 A1 | 7/2009 | | |
| DE | 102008033106 A1 | 1/2010 | | |
| EP | 1216684 A1 | 6/2002 | | |
| EP | 2105128 A2 | 9/2009 | | |
| IL | WO 2011045794 A1 * | 4/2011 | | A61K 8/042 |
| WO | 2007099434 A2 | 9/2007 | | |

* cited by examiner

Primary Examiner — Nannette Holloman
(74) Attorney, Agent, or Firm — Lorenz & Kopf, LLP

(57) ABSTRACT

Agents for cosmetically treating keratin-containing fibers, in particular human hair, contain in a cosmetically acceptable carrier (i) at least one ester of formula (I), where $R^1$ stands for a linear or branched ($C_2$-$C_{30}$) alkyl group, a linear or branched ($C_8$-$C_{30}$) alkenyl group, a ($C_2$-$C_{30}$) alkylpoly (oxyethylene) group, an optionally substituted aryl group, an optionally substituted aryl($C_1$-$C_4$)alkyl group or a ($C_2$-$C_6$) hydroxyalkyl group, and $R^2$ stands for an optionally substituted aryl group, a linear or branched ($C_8$-$C_{30}$) alkyl group, a linear or branched ($C_8$-$C_{30}$) alkenyl group, an optionally substituted aryl ($C_1$-$C_4$) alkyl group, an optionally substituted aryl ($C_2$-$C_4$) alkenyl group or a ($C_{2-6}$) hydroxyalkyl group, and (ii) at least one oil selected from at least one compound of the group comprising silicones and paraffin oil, which are particularly suited in the form of a spray mist for giving shine to keratin-containing fibers, in particular human hair.

11 Claims, No Drawings

SHINE-PRODUCING HAIR TREATMENT AGENT

CROSS REFERENCE TO RELATED APPLICATIONS

The present disclosure is a U.S. National Stage entry under 35 U.S.C. §371 based on International Application No. PCT/EP2012/070921, filed Oct. 23, 2012 which was published under PCT Article 21(2) and which claims priority to German Patent Application No. DE 10 2011 087 233.7 filed on Nov. 28, 2011, which is incorporated herein by reference in its entirety.

TECHNICAL FIELD

The technical field relates to agents for cosmetic treatment of keratin-containing fibers, in particular for cosmetic hair treatment.

BACKGROUND

"Keratin-containing fibers" are understood in principle as all animal hair, e.g. wool, horsehair, angora wool, furs, human hair, feathers, and products or textiles produced therefrom. Preferably, however, the keratinic fibers are human hairs.

Human hair is constantly exposed to environmental influences such as UV radiation, heat, water, and mechanical tearing. In addition, in the context of a cosmetic hair treatment the hair often experiences a modification of the hair surface (e.g. by deposition of care-providing substances) or of the hair structure (e.g. as a result of care-providing substances or chemical modification in the context of a reducing or oxidizing hair treatment). The use of a dry shampoo, for example, produces not only a removal of dirt but also a reduction in sebum on the hair surface which, together with the deposition of fatty substances on the hair, imparts to the hair a slightly dull appearance. A further example is offered by a cosmetic leave-on hair treatment in which the cosmetic agent is not rinsed off the hair after application and remains on the hair fibers. The leave-on cosmetic has an influence on the visual impression of the hair as a result of its presence on the hair surface. In order to compensate for possible undesired effects, for example negative impacts on the natural hair shine, it is advisable to employ a cosmetic having, for example, shine-imparting active agents.

The shine-imparting active agents become deposited mostly on the surface of the hair in the context of a leave-on utilization, which on the one hand results in the desired shine. On the other hand, this leave-on shine utilization can run counter to the effect of the previously or simultaneously applied cosmetic agent. When oils are used as shine active agents, for example, the oils can weigh down the hair. A temporary hair setting operation using setting polymers can, for example, be less effective due to the presence of shine active agents that weigh down the hair, since the weighed-down hair straightens out more quickly under its own weight, and the imparted hairstyle is quickly lost. This can additionally be promoted by a property of the shine active agent by which it softens the setting polymer film. The direct combination of shine active agent and dry shampoo can moreover decrease the effectiveness of the washing action of the dry shampoo.

Accordingly, it is desirable to provide a cosmetic agent for caring for keratinic fibers that brings about outstanding shine on the keratin-containing fibers without weighing down the fibers.

SUMMARY

Agents for cosmetic treatment of keratin-containing fibers, aerosol sprays containing such agents, and methods of imparting shine on keratin-containing fibers using such agents are provided. In accordance with an exemplary embodiment, an agent for cosmetic treatment of keratin-containing fibers contains in a cosmetically acceptable carrier:
at least one ester of formula (I)

in which
$R^1$ signifies a linear or branched ($C_2$ to $C_{30}$) alkyl group, a linear or branched ($C_8$ to $C_{30}$) alkenyl group, a ($C_2$ to $C_{30}$) alkylpoly(oxyethylene) group, an optionally substituted aryl group, an optionally substituted aryl-($C_1$ to $C_4$) alkyl group, or a ($C_2$ to $C_6$) hydroxyalkyl group, and
$R^2$ signifies an optionally substituted aryl group, a linear or branched ($C_8$ to $C_{30}$) alkyl group, a linear or branched ($C_8$ to $C_{30}$) alkenyl group, an optionally substituted aryl-($C_1$ to $C_4$) alkyl group, an optionally substituted aryl-($C_2$ to $C_4$) alkenyl group, or a ($C_2$ to $C_6$) hydroxyalkyl group,
and
an oil chosen from silicones and paraffin oil.

In accordance with another exemplary embodiment, an aerosol spray in an aerosol container having a spraying apparatus contains a cosmetic agent comprising in a cosmetically acceptable carrier:
(i) at least one ester of formula (I)

in which
$R^1$ signifies a linear or branched ($C_2$ to $C_{30}$) alkyl group, a linear or branched ($C_8$ to $C_{30}$) alkenyl group, a ($C_2$ to $C_{30}$) alkylpoly(oxyethylene) group, an optionally substituted aryl group, an optionally substituted aryl-($C_1$ to $C_4$) alkyl group, or a ($C_2$ to $C_6$) hydroxyalkyl group, and
$R^2$ signifies an optionally substituted aryl group, a linear or branched ($C_8$ to $C_{30}$) alkyl group, a linear or branched ($C_8$ to $C_{30}$) alkenyl group, an optionally substituted aryl-($C_1$ to $C_4$) alkyl group, an optionally substituted aryl-($C_2$ to $C_4$) alkenyl group, or a ($C_2$ to $C_6$) hydroxyalkyl group,
and
(ii) an oil chosen from silicones and paraffin oil, and
a propellant.

In accordance with a further exemplary embodiment, a method of imparting shine on keratin-containing fibers includes applying to the keratin-containing fibers a dry shampoo and/or a cosmetic agent containing at least one polymer having a setting effect and subsequently applying to the keratin-containing fibers an agent containing in a cosmetically acceptable carrier:

(i) at least one ester of formula (I)

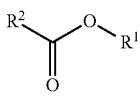
(I)

in which
- $R^1$ signifies a linear or branched ($C_2$ to $C_{30}$) alkyl group, a linear or branched ($C_8$ to $C_{30}$) alkenyl group, a ($C_2$ to $C_{30}$) alkylpoly(oxyethylene) group, an optionally substituted aryl group, an optionally substituted aryl-($C_1$ to $C_4$) alkyl group, or a ($C_2$ to $C_6$) hydroxyalkyl group, and
- $R^2$ signifies an optionally substituted aryl group, a linear or branched ($C_8$ to $C_{30}$) alkyl group, a linear or branched ($C_8$ to $C_{30}$) alkenyl group, an optionally substituted aryl-($C_1$ to $C_4$) alkyl group, an optionally substituted aryl-($C_2$ to $C_4$) alkenyl group, or a ($C_2$ to $C_6$) hydroxyalkyl group, and
an oil chosen from silicones and paraffin oil.

DETAILED DESCRIPTION

In accordance with an exemplary embodiment, a cosmetic agent for caring for keratinic fibers that brings about outstanding shine on the keratin-containing fibers without weighing down the fibers is herein provided. It has now been found that this is achieved by means of a combination of special oils with special esters, especially when they are applied as a fine spray mist onto the fibers. A further result has been that the treated fibers are better able to disentangle, which is reflected in improved combability of the keratinic fibers.

A first embodiment is therefore an agent for cosmetic treatment of keratin-containing fibers, in particular human hair, containing in a cosmetically acceptable carrier (i) at least one ester of formula (I)

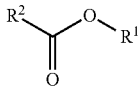
(I)

in which
- $R^1$ signifies a linear or branched ($C_2$ to $C_{30}$) alkyl group, a linear or branched ($C_8$ to $C_{30}$) alkenyl group, a ($C_2$ to $C_{30}$) alkylpoly(oxyethylene) group, an optionally substituted aryl group, an optionally substituted aryl-($C_1$ to $C_4$) alkyl group, or a ($C_2$ to $C_6$) hydroxyalkyl group, and
- $R^2$ signifies an optionally substituted aryl group, a linear or branched ($C_8$ to $C_{30}$) alkyl group, a linear or branched ($C_8$ to $C_{30}$) alkenyl group, an optionally substituted aryl-($C_1$ to $C_4$) alkyl group, an optionally substituted aryl-($C_2$ to $C_4$) alkenyl group, or a ($C_2$ to $C_6$) hydroxyalkyl group, and (i) at least one oil selected from at least one compound of the group constituted from silicones and paraffin oil.

Examples of linear or branched ($C_2$ to $C_{30}$) alkyl groups useful herein are ethyl, propyl, isopropyl, butyl, tert-butyl, 2-ethylhexyl, dodecanyl, tridecanyl, tetradecanyl, pentadecanyl, hexadecanyl, octadecanyl, isostearyl, behenyl. Examples of linear or branched ($C_8$ to $C_{30}$) alkyl groups useful herein are 2-ethylhexyl, decanyl, dodecanyl, tridecanyl, tetradecanyl, pentadecanyl, hexadecanyl, octadecanyl, isostearyl, behenyl. Examples of linear or branched ($C_8$ to $C_{30}$) alkenyl groups are oleyl, linolenyl, linolyl. The aryl structural units of the aryl group, aryl-($C_1$ to $C_4$) alkyl group, and aryl-($C_2$ to $C_4$) alkenyl group can carry substituents. Preferred substituents are hydroxy, amino, ($C_1$ to $C_4$) alkylamino, di-($C_1$ to $C_4$) alkylamino, ($C_1$ to $C_4$) alkyl, ($C_1$ to $C_4$) alkoxy, ($C_1$ to $C_4$) alkoxycarbonyl. Examples of optionally substituted aryl groups are phenyl, 2-hydroxyphenyl, 2-methoxyphenyl, naphthyl, 7-hydroxynaphthyl, 5-hydroxynaphthyl.

Examples of aryl-($C_1$ to $C_4$) alkyl groups useful herein are benzyl, 2-phenylethyl. Examples of aryl-($C_2$ to $C_4$) alkenyl groups useful herein are styryl.

Examples of ($C_2$ to $C_6$) hydroxyalkyl groups useful herein are 1-hydroxyethyl, 2-hydroxyethyl, 2-hydroxypropyl, 2-hydroxybutyl, 3-hydroxybutyl, 3-hydroxy-2-methylpropyl.

Examples of a preferred a ($C_2$ to $C_{30}$) alkylpoly(oxyethylene).

It is preferred if the agents contemplated herein are present as a spray mist, in particular as a spray mist produced with the aid of a propellant. It is preferred if, in accordance with formula (I), at least one of the groups $R^1$ and $R^2$ is an optionally substituted aryl group. It is preferred in turn in this context if $R^2$ denotes an optionally substituted aryl group, in particular optionally substituted phenyl. Preferred substituents for the aryl group or phenyl group are hydroxy, amino, ($C_1$ to $C_4$) alkylamino, di-($C_1$ to $C_4$) alkylamino, ($C_1$ to $C_4$) alkyl, ($C_1$ to $C_4$) alkoxy, ($C_1$ to $C_4$) alkoxycarbonyl.

In an exemplary embodiment, the agent contemplated herein contains, as an ester of the above formula (I), at least one ester of formula (I-a)

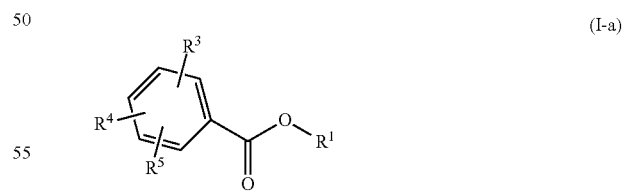
(I-a)

in which
- $R^1$ denotes a linear or branched ($C_3$ to $C_{24}$) alkyl group, a linear or branched ($C_6$ to $C_{24}$) alkenyl group, an optionally substituted aryl group, an optionally substituted aryl-($C_1$ to $C_4$) alkyl group, or a ($C_2$ to $C_6$) hydroxyalkyl group, and
- $R^3$, $R^4$, and $R^5$ mutually independently denote a hydrogen atom, hydroxy, amino, ($C_1$ to $C_4$) alkylamino, di-($C_1$ to $C_4$) alkylamino, ($C_1$ to $C_4$) alkyl, ($C_1$ to $C_4$) alkoxy, ($C_1$ to $C_4$) alkoxycarbonyl, or two of the residues form, together with the remainder of the molecule, a five- or six-membered ring.

According to formula (I) and formula (I-a), $R^1$ preferably denotes a linear or branched ($C_4$ to $C_{18}$) alkyl group, a linear or branched ($C_8$ to $C_{22}$) alkenyl group, an optionally substituted aryl group, an optionally substituted aryl-($C_1$ to $C_4$) alkyl group, or a ($C_2$ to $C_6$) hydroxyalkyl group.

Preferably the residues $R^3$, $R^4$ and $R^5$ according to formula (I-a) mutually independently denote a hydrogen atom, hydroxy, amino, ($C_1$ to $C_4$) alkylamino, di-($C_1$ to $C_4$) alkylamino, ($C_1$ to $C_4$) alkyl, ($C_1$ to $C_4$) alkoxy, ($C_1$ to $C_4$) alkoxycarbonyl.

Particularly preferably, the residues $R^3$, $R^4$, and $R^5$ according to formula (I-a) mutually independently denote a hydrogen atom, hydroxy, amino, N-methylamino, N-ethylamino, N,N-dimethylamino, N,N-diethylamino, methyl, ethyl, isopropyl, methoxy, ethoxy, methoxycarbonyl, or ethoxycarbonyl.

A very particularly preferred ester of formula (I) is selected from an ester of benzoic acid with a ($C_{10}$ to $C_{18}$) alkanol, in particular from an ester of benzoic acid with a ($C_{12}$ to $C_{15}$) alkanol. Such esters can be obtained, for example, from the Finetex company under the trade name Finsolv® TN (INCI name: C12-15 Alkyl Benzoate). The aforesaid esters of component (i), in particular the preferably recited aforesaid esters of component (i), are contained in the agent contemplated herein in a quantity from 0.5 to 15.0 wt %, in particular from 1.0 to 10.0 wt %, with reference to the total weight of the agent.

As a further component (ii) the agent contemplated herein obligatorily contains at least one aforesaid oil. An "oil" is, for purposes of the invention, a substance liquid at 20° C. of which no more than 0.5 g dissolves in 100 g water at 20° C. Serving as a list for selection of at least one particularly preferred suitable oil are those oils which have a viscosity from 0.2 to 2 mPas, in particular from 0.5 to 1 mPas measured at 20° C. by rotational viscometry, and are selected from silicones, paraffin oil, or mixtures of the two.

Suitable paraffin oils are known to one skilled in the art. Oils of isoparaffin are also included thereamong.

Particularly preferred agents are characterized in that they contain as component (ii) at least one silicone oil of formula (Si-1)

$(CH_3)_3Si$—$[O$—$Si(CH_3)_2]_x$—$O$—$Si(CH_3)_3$      (Si-1),

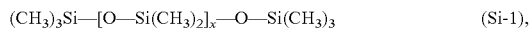

in which x denotes a number from 0 to 100, preferably from 0 to 50, more preferably from 0 to 20, and in particular 0 to 10. These silicones are referred to according to INCI nomenclature as Hexamethyldisiloxanes (formula (Si-1) where x=0), Trisiloxanes (formula (Si-1) where x=1), and Dimethicones (formula (Si-1) where x=2 to 100). At least one compound from among $(CH_3)_3Si$—$O$—$Si(CH_3)_3$, $(CH_3)_3Si$—$O$—$(CH_3)_2Si$—$O$—$Si(CH_3)_3$, $(CH_3)_3Si$—$[O$—$(CH_3)_2Si]_2$—$O$—$Si(CH_3)_3$, $(CH_3)_3Si$—$[O$—$(CH_3)_2Si]_3$—$O$—$Si(CH_3)_3$, $(CH_3)_3Si$—$[O$—$(CH_3)_2Si]_4$—$O$—$Si(CH_3)_3$, $(CH_3)_3Si$—$[O$—$(CH_3)_2Si]_5$—$O$—$Si(CH_3)_3$, $(CH_3)_3Si$—$[O$—$(CH_3)_2Si]_6$—$O$—$Si(CH_3)_3$, $(CH_3)_3Si$—$[O$—$(CH_3)_2Si]_7$—$O$—$Si(CH_3)_3$, $(CH_3)_3Si$—$[O$—$(CH_3)_2Si]_8$—$O$—$Si(CH_3)_3$, $(CH_3)_3Si$—$[O$—$(CH_3)_2Si]_9$—$O$—$Si(CH_3)_3$, $(CH_3)_3Si$—$[O$—$(CH_3)_2Si]_{10}$—$O$—$Si(CH_3)_3$, $(CH_3)_3Si$—$[O$—$(CH_3)_2Si]_{11}$—$Si(CH_3)_3$, $(CH_3)_3Si$—$[O$—$(CH_3)_2Si]_{12}$—$O$—$Si(CH_3)_3$, $(CH_3)_3Si$—$[O$—$(CH_3)_2Si]_{13}$—$O$—$Si(CH_3)_3$, $(CH_3)_3Si$—$[O$—$(CH_3)_2Si]_{14}$—$O$—$Si(CH_3)_3$, $(CH_3)_3Si$—$[O$—$(CH_3)_2Si]_{15}$—$O$—$Si(CH_3)_3$, $(CH_3)_3Si$—$[O$—$(CH_3)_2Si]_{16}$—$O$—$Si(CH_3)_3$, $(CH_3)_3Si$—$[O$—$(CH_3)_2Si]_{17}$—$O$—$Si(CH_3)_3$, $(CH_3)_3Si$—$[O$—$(CH_3)_2Si]_{18}$—$O$—$Si(CH_3)_3$, $(CH_3)_3Si$—$[O$—$(CH_3)_2Si]_{19}$—$O$—$Si(CH_3)_3$, $(CH_3)_3Si$—$[O$—$(CH_3)_2Si]_{20}$—$O$—$Si(CH_3)_3$ is preferably used herein as a silicone of formula (Si-1); $(CH_3)_3Si$—$O$—$Si(CH_3)_3$ and/or $(CH_3)_3Si$—$O$—$(CH_3)_2Si$—$O$—$Si(CH_3)_3$ and/or $(CH_3)_3Si$—$[O$—$(CH_3)_2Si]_2$—$O$—$Si(CH_3)_3$ are particularly preferred. $(CH_3)_3Si$—$O$—$(CH_3)_2Si$—$O$—$Si(CH_3)_3$ is a very particularly preferred oil.

Mixtures of the aforementioned silicones can of course also be contained in the preferred agents contemplated herein.

Particularly preferred silicones of formula (Si-1) usable herein have viscosities from about 0.2 to about 2 $mm^2s^{-1}$ at 20° C., aforesaid silicones having viscosities from about 0.5 to about 1 $mm^2s^{-1}$ being particularly preferred. The viscosities are determined at 20° C. by rotational viscometry. The aforesaid oils of component (ii), in particular the preferably recited aforesaid oils of component (ii), are contained in the agent in a quantity from about 0.5 to about 20.0 wt %, in particular from about 1.0 to about 15.0 wt %, with reference to the total weight of the agent.

The embodiments (A) to (H) serve as very particularly preferred embodiments of the agent contemplated herein:

(A): An agent for cosmetic treatment of keratin-containing fibers, in particular human hair, containing in a cosmetically acceptable carrier (i) at least one ester of formula (I)

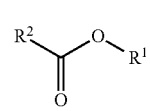

(I)

in which
$R^1$ signifies a linear or branched ($C_2$ to $C_{30}$) alkyl group, a linear or branched ($C_8$ to $C_{30}$) alkenyl group, a ($C_2$ to $C_{30}$) alkylpoly(oxyethylene) group, an optionally substituted aryl group, an optionally substituted aryl-($C_1$ to $C_4$) alkyl group, or a ($C_2$ to $C_6$) hydroxyalkyl group, and
$R^2$ signifies a linear or branched ($C_8$ to $C_{30}$) alkyl group, a linear or branched ($C_8$ to $C_{30}$) alkenyl group, an optionally substituted aryl group, an optionally substituted aryl-($C_1$ to $C_4$) alkyl group, an optionally substituted aryl-($C_2$ to $C_4$) alkenyl group, or a ($C_2$ to $C_6$) hydroxyalkyl group,
and
(ii) at least one silicone oil.

(B): An agent for cosmetic treatment of keratin-containing fibers, in particular human hair, containing in a cosmetically acceptable carrier:

(i) at least one ester of formula (I-a)

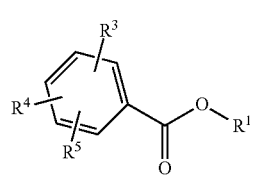

(I-a)

in which
$R^1$ denotes a linear or branched ($C_3$ to $C_{24}$) alkyl group, a linear or branched ($C_6$ to $C_{24}$) alkenyl group, an optionally substituted aryl group, an optionally substituted aryl-($C_1$ to $C_4$) alkyl group, or a ($C_2$ to $C_6$) hydroxyalkyl group, and $R^3$, $R^4$, and $R^5$ mutually independently denote a hydrogen atom, hydroxy, amino, ($C_1$ to $C_4$) alkylamino, di-($C_1$ to $C_4$) alkylamino, ($C_1$ to $C_4$) alkyl, ($C_1$ to $C_4$) alkoxy, ($C_1$ to $C_4$) alkoxycarbonyl, or two of the residues form, together with the remainder of the molecule, a five- or six-membered ring, and (ii) at least one silicone oil.

(C): An agent for cosmetic treatment of keratin-containing fibers, in particular human hair, containing in a cosmetically acceptable carrier (i) at least one ester of formula (I)

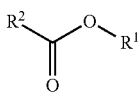
(I)

in which $R^1$ signifies a linear or branched ($C_2$ to $C_{30}$) alkyl group, a linear or branched ($C_8$ to $C_{30}$) alkenyl group, a ($C_2$ to $C_{30}$) alkylpoly(oxyethylene) group, an optionally substituted aryl group, an optionally substituted aryl-($C_1$ to $C_4$) alkyl group, or a ($C_2$ to $C_6$) hydroxyalkyl group, and $R^2$ signifies a linear or branched ($C_8$ to $C_{30}$) alkyl group, a linear or branched ($C_8$ to $C_{30}$) alkenyl group, an optionally substituted aryl group, an optionally substituted aryl-($C_1$ to $C_4$) alkyl group, an optionally substituted aryl-($C_2$ to $C_4$) alkenyl group, or a ($C_2$ to $C_6$) hydroxyalkyl group, and (ii) at least one silicone oil of formula (Si-1)

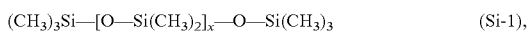
(Si-1), in which x denotes a number from 0 to 100, preferably from 0 to 50, more preferably from 0 to 20, and in particular 0 to 10.

(D): An agent for cosmetic treatment of keratin-containing fibers, in particular human hair, containing in a cosmetically acceptable carrier:

(i) at least one ester of formula (I-a)

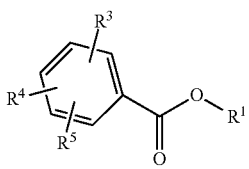
(I-a)

in which $R^1$ denotes a linear or branched ($C_3$ to $C_{24}$) alkyl group, a linear or branched ($C_6$ to $C_{24}$) alkenyl group, an optionally substituted aryl group, an optionally substituted aryl-($C_1$ to $C_4$) alkyl group, or a ($C_2$ to $C_6$) hydroxyalkyl group, and $R^3$, $R^4$, and $R^5$ mutually independently denote a hydrogen atom, hydroxy, amino, ($C_1$ to $C_4$) alkylamino, di-($C_1$ to $C_4$) alkylamino, ($C_1$ to $C_4$) alkyl, ($C_1$ to $C_4$) alkoxy, ($C_1$ to $C_4$) alkoxycarbonyl, or two of the residues form, together with the remainder of the molecule, a five- or six-membered ring, and (ii) at least one silicone oil of formula (Si-1)

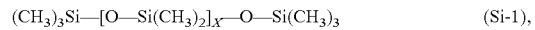
(Si-1), in which x denotes a number from 0 to 100, preferably from 0 to 50, more preferably from 0 to 20, and in particular 0 to 10.

(E): An agent for cosmetic treatment of keratin-containing fibers, in particular human hair, containing in a cosmetically acceptable carrier, based on the total weight of the agent, (i) about 1.0 to about 10.0 wt % of at least one ester of formula (I)

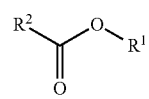
(I)

in which $R^1$ signifies a linear or branched ($C_2$ to $C_{30}$) alkyl group, a linear or branched ($C_8$ to $C_{30}$) alkenyl group, a ($C_2$ to $C_{30}$) alkylpoly(oxyethylene) group, an optionally substituted aryl group, an optionally substituted aryl-($C_1$ to $C_4$) alkyl group, or a ($C_2$ to $C_6$) hydroxyalkyl group, and $R^2$ signifies a linear or branched ($C_8$ to $C_{30}$) alkyl group, a linear or branched ($C_8$ to $C_{30}$) alkenyl group, an optionally substituted aryl group, an optionally substituted aryl-($C_1$ to $C_4$) alkyl group, an optionally substituted aryl-($C_2$ to $C_4$) alkenyl group, or a ($C_2$ to $C_6$) hydroxyalkyl group, and (ii) about 1.0 to about 15.0 wt % of at least one silicone oil.

(F): An agent for cosmetic treatment of keratin-containing fibers, in particular human hair, containing in a cosmetically acceptable carrier:

(i) about 1.0 to about 10.0 wt % of at least one ester of formula (I-a)

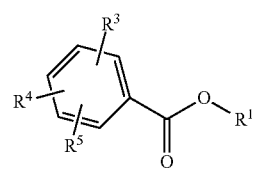
(I-a)

in which $R^1$ denotes a linear or branched ($C_3$ to $C_{24}$) alkyl group, a linear or branched ($C_6$ to $C_{24}$) alkenyl group, an optionally substituted aryl group, an optionally substituted aryl-($C_1$ to $C_4$) alkyl group, or a ($C_2$ to $C_6$) hydroxyalkyl group, and $R^3$, $R^4$, and $R^5$ mutually independently denote a hydrogen atom, hydroxy, amino, ($C_1$ to $C_4$) alkylamino, di-($C_1$ to $C_4$) alkylamino, ($C_1$ to $C_4$) alkyl, ($C_1$ to $C_4$) alkoxy, ($C_1$ to $C_4$) alkoxycarbonyl, or two of the residues form, together with the remainder of the molecule, a five- or six-membered ring, and (ii) about 1.0 to about 15.0 wt % of at least one silicone oil.

(G): An agent for cosmetic treatment of keratin-containing fibers, in particular human hair, containing in a cosmetically acceptable carrier
  (i) about 1.0 to about 10.0 wt % of at least one ester of formula (I)

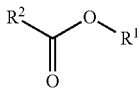
(I)

in which
  $R^1$ signifies a linear or branched ($C_2$ to $C_{30}$) alkyl group, a linear or branched ($C_8$ to $C_{30}$) alkenyl group, a ($C_2$ to $C_{30}$) alkylpoly(oxyethylene) group, an optionally substituted aryl group, an optionally substituted aryl-($C_1$ to $C_4$) alkyl group, or a ($C_2$ to $C_6$) hydroxyalkyl group, and
  $R^2$ signifies a linear or branched ($C_8$ to $C_{30}$) alkyl group, a linear or branched ($C_8$ to $C_{30}$) alkenyl group, an optionally substituted aryl group, an optionally substituted aryl-($C_1$ to $C_4$) alkyl group, an optionally substituted aryl-($C_2$ to $C_4$) alkenyl group, or a ($C_2$ to $C_6$) hydroxyalkyl group,
  and
  (ii) about 1.0 to about 15 wt % of at least one silicone oil of formula (Si-1)

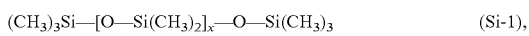
(Si-1), in which x denotes a number from 0 to 100, preferably from 0 to 50, more preferably from 0 to 20, and in particular 0 to 10.

(H): An agent for cosmetic treatment of keratin-containing fibers, in particular human hair, containing in a cosmetically acceptable carrier:
  (i) about 1.0 to about 10.0 wt % of at least one ester of formula (I-a)

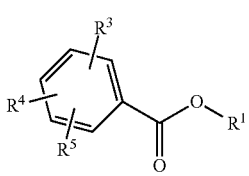
(I-a)

in which
  $R^1$ denotes a linear or branched ($C_3$ to $C_{24}$) alkyl group, a linear or branched ($C_6$ to $C_{24}$) alkenyl group, an optionally substituted aryl group, an optionally substituted aryl-($C_1$ to $C_4$) alkyl group, or a ($C_2$ to $C_6$) hydroxyalkyl group, and
  $R^3$, $R^4$, and $R^5$ mutually independently denote a hydrogen atom, hydroxy, amino, ($C_1$ to $C_4$) alkylamino, di-($C_1$ to $C_4$) alkylamino, ($C_1$ to $C_4$) alkyl, ($C_1$ to $C_4$) alkoxy, ($C_1$ to $C_4$) alkoxycarbonyl, or two of the residues form, together with the remainder of the molecule, a five- or six-membered ring, and
  (ii) about 1.0 to about 15 wt % of at least one silicone oil of formula (Si-1)

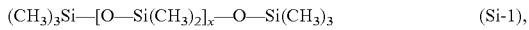
(Si-1), in which x denotes a number from 0 to 100, preferably from 0 to 50, more preferably from 0 to 20, and in particular 0 to 10.

In the context of the preferred embodiments, in particular embodiments (A) to (H), it is preferred in turn if they are present as a spray mist.

The agents contemplated herein contain the ingredients or active agents in a cosmetically acceptable carrier. Preferred cosmetically acceptable carriers are alcoholic or aqueous alcoholic media. The latter preferably comprise at most about 10 wt % water, based on the complete agent. In the context of a preferred embodiment of the agent, the agent additionally contains at least one alcohol that comprises 2 to 6 carbon atoms and 1 to 3 hydroxyl groups. This additional alcohol is in turn preferably selected from at least one compound of the group that is constituted from ethanol, isopropanol, ethylene glycol, 1,2-propylene glycol, 1,3-propylene glycol, glycerol, n-butanol, 1,3-butylene glycol. Very particularly preferred alcohols are ethanol, isopropanol, and a mixture thereof.

It is particularly preferred if the aforesaid additional alcohol having at least 2 to 6 carbon atoms is contained in a quantity from about 30.0 to about 70.0 wt %, in particular from about 40.0 to about 60.0 wt %, based on the weight of the agent.

The embodiments (J) to (M) serve as very particularly preferred agents contemplated herein:

(J): An agent for cosmetic treatment of keratin-containing fibers, in particular human hair, containing, based on the total weight of the agent,
  (i) about 1.0 to about 10.0 wt % of at least one ester of formula (I)

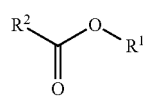
(I)

in which
  $R^1$ signifies a linear or branched ($C_2$ to $C_{30}$) alkyl group, a linear or branched ($C_8$ to $C_{30}$) alkenyl group, a ($C_2$ to $C_{30}$) alkylpoly(oxyethylene) group, an optionally substituted aryl group, an optionally substituted aryl-($C_1$ to $C_4$) alkyl group, or a ($C_2$ to $C_6$) hydroxyalkyl group, and
  $R^2$ signifies a linear or branched ($C_8$ to $C_{30}$) alkyl group, a linear or branched ($C_8$ to $C_{30}$) alkenyl group, an optionally substituted aryl group, an optionally substituted aryl-($C_1$ to $C_4$) alkyl group, an optionally substituted aryl-($C_2$ to $C_4$) alkenyl group, or a ($C_2$ to $C_6$) hydroxyalkyl group,
  and
  (ii) about 1.0 to about 15.0 wt % of at least one silicone oil, and
  (iii) about 30.0 to about 70.0 wt % (in particular about 40 to about 60 wt %) of at least one alcohol that comprises 2 to 6 carbon atoms and 1 to 3 hydroxyl groups, in particular ethanol, as a constituent of the cosmetically acceptable carrier.

(K): An agent for cosmetic treatment of keratin-containing fibers, in particular human hair, containing, based on the total weight of the agent:
  (i) about 1.0 to about 10.0 wt % of at least one ester of formula (I-a)

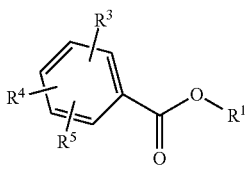

(I-a)

in which

R¹ denotes a linear or branched ($C_3$ to $C_{24}$) alkyl group, a linear or branched ($C_6$ to $C_{24}$) alkenyl group, an optionally substituted aryl group, an optionally substituted aryl-($C_1$ to $C_4$) alkyl group, or a ($C_2$ to $C_6$) hydroxyalkyl group, and R³, R⁴, and R⁵ mutually independently denote a hydrogen atom, hydroxy, amino, ($C_1$ to $C_4$) alkylamino, di-($C_1$ to $C_4$) alkylamino, ($C_1$ to $C_4$) alkyl, ($C_1$ to $C_4$) alkoxy, ($C_1$ to $C_4$) alkoxycarbonyl, or two of the residues form, together with the remainder of the molecule, a five- or six-membered ring, and (ii) about 1.0 to about 15.0 wt % of at least one silicone oil, and (iii) about 30.0 to about 70.0 wt % (in particular about 40 to about 60 wt %) of at least one alcohol that comprises 2 to 6 carbon atoms and 1 to 3 hydroxyl groups, in particular ethanol, as a constituent of the cosmetically acceptable carrier.

(L): An agent for cosmetic treatment of keratin-containing fibers, in particular human hair, containing, based on the total weight of the agent:

(i) about 1.0 to about 10.0 wt % at least one ester of formula (I)

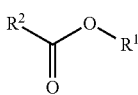

(I)

in which

R¹ signifies a linear or branched ($C_2$ to $C_{30}$) alkyl group, a linear or branched ($C_8$ to $C_{30}$) alkenyl group, a ($C_2$ to $C_{30}$) alkylpoly(oxyethylene) group, an optionally substituted aryl group, an optionally substituted aryl-($C_1$ to $C_4$) alkyl group, or a ($C_2$ to $C_6$) hydroxyalkyl group, and R² signifies a linear or branched ($C_8$ to $C_{30}$) alkyl group, a linear or branched ($C_8$ to $C_{30}$) alkenyl group, an optionally substituted aryl group, an optionally substituted aryl-($C_1$ to $C_4$) alkyl group, an optionally substituted aryl-($C_2$ to $C_4$) alkenyl group, or a ($C_2$ to $C_6$) hydroxyalkyl group, and (ii) about 1.0 to about 15.0 wt % of at least one silicone oil of formula (Si-1)

$(CH_3)_3Si—[O—Si(CH_3)_2]_x—O—Si(CH_3)_3$ (Si-1), in which x denotes a number from 0 to 100, preferably from 0 to 50, more preferably from 0 to 20, and in particular 0 to 10 and (iii) about 30.0 to about 70.0 wt % (in particular about 40 to about 60 wt %) of at least one alcohol that comprises 2 to 6 carbon atoms and 1 to 3 hydroxyl groups, in particular ethanol, as a constituent of the cosmetically acceptable carrier.

(M): An agent for cosmetic treatment of keratin-containing fibers, in particular human hair, containing, based on the total weight of the agent:

(i) about 1.0 to about 10.0 wt % of at least one ester of formula (I-a)

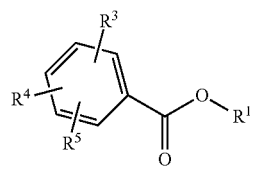

(I-a)

in which

R¹ denotes a linear or branched ($C_3$ to $C_{24}$) alkyl group, a linear or branched ($C_6$ to $C_{24}$) alkenyl group, an optionally substituted aryl group, an optionally substituted aryl-($C_1$ to $C_4$) alkyl group, or a ($C_2$ to $C_6$) hydroxyalkyl group, and R³, R⁴, and R⁵ mutually independently denote a hydrogen atom, hydroxy, amino, ($C_1$ to $C_4$) alkylamino, di-($C_1$ to $C_4$) alkylamino, ($C_1$ to $C_4$) alkyl, ($C_1$ to $C_4$) alkoxy, ($C_1$ to $C_4$) alkoxycarbonyl, or two of the residues form, together with the remainder of the molecule, a five- or six-membered ring, and and (ii) about 1.0 to about 15.0 wt % of at least one silicone oil of formula (Si-1)

$(CH_3)_3Si—[O—Si(CH_3)_2]_x—O—Si(CH_3)_3$ (Si-1), in which x denotes a number from 0 to 100, preferably from 0 to 50, more preferably from 0 to 20, and in particular 0 to 10 and (iii) about 30.0 to about 70.0 wt % (in particular about 40 to about 60 wt %) of at least one alcohol that comprises 2 to 6 carbon atoms and 1 to 3 hydroxyl groups, in particular ethanol, as a constituent of the cosmetically acceptable carrier.

In the context of the preferred embodiments (J) to (M), it is preferred in turn if they are present as a spray mist, in particular as a spray mist produced with the aid of a propellant.

Organic solvents or a mixture of solvents having a boiling point below 400° C. can be contained as additional co-solvents, in a quantity from about 0.1 to about 15 weight percent, preferably from about 1 to about 10 weight percent, based on the total agent. Unbranched or branched hydrocarbons such as pentane, hexane, isopentane, and cyclic hydrocarbons such as cyclopentane and cyclohexane, are particularly suitable as additional co-solvents.

Optionally, the agents contemplated herein can additionally contain at least one setting polymer. The optionally added setting polymers are preferably anionic, amphoteric, zwitterionic, or nonionic, particularly preferably anionic. The setting polymers are contained usually in a quantity from about 0.1 wt % to about 20.0 wt %, particularly preferably from about 0.2 wt % to about 10.0 wt %, based in each case on the weight of the agent.

"Polymers" are understood according to the present invention as compounds that are different from the compounds of components (i) and (ii) of the agent according to the present invention and have a molecular weight of at least 10,000 g/mol. Polymers are constructed from a plurality of molecules in which one type or several types of atoms or atom groupings (so-called "constituent units," "basic modules," or "repeating units") are repeatedly serially arranged. Polymers are obtained by polyreaction, which latter can be accomplished artificially (i.e. synthetically) or naturally.

"Film-forming polymers" are to be understood as those polymers which, upon drying, leave behind a continuous film on the skin, hair, or nails. Film-formers of this kind can be used in a very wide variety of cosmetic products such as, for example, face masks, make-up, hair setting agents, hair sprays, hair gels, hair waxes, hair therapies, shampoos, or nail polishes. Particularly preferred are those polymers which possess sufficient solubility in water or water/alcohol mixtures to be present in completely dissolved form in the agent. The film-forming polymers can be of synthetic or natural origin. "Film-forming polymers" are furthermore understood as used herein as those polymers which, when used in a about 0.01 to about 20 wt % aqueous, alcoholic, or aqueous alcoholic solution, are capable of depositing a transparent polymer film onto the hair.

Setting polymers contribute to the hold, and/or to buildup of the hair volume and hair fullness, of the overall hairstyle. These polymers are at the same time also film-forming polymers and are therefore generally typical substances for shape-imparting hair-treatment agents such as hair setting agents, hair foams, hair waxes, hair sprays. It is certainly possible for film formation to be localized, and for only a few fibers to be connected to one another.

The so-called "curl retention" test is often used as a test method for the setting effect of a polymer.

Anionic polymers are polymers that carry at least one anionic group (preferably *—COO$^-$ and/or *—SO$_3^-$) and no cationic group (e.g. *—N$^+$Me$_3$ or *—N$^+$H$_3$). Anionic setting polymers are contained in the agent contemplated herein preferably in a quantity from about 0.1 wt % to about 20 wt %, particularly preferably from about 0.5 wt % to about 15 wt %, very particularly preferably from about 1.0 wt % to about 10.0 wt %, and most preferably from about 2.0 wt % to about 6.0 wt %, based in each case on the weight of the composition.

Anionic polymers preferably usable herein have a molecular weight from about 10,000 to about 250,000 g/mol, in particular about 20,000 to about 200,000 g/mol.

It is preferred if the anionic setting polymer contains at least one structural unit of formula (S1) that is selected from at least one structural unit of formulas (S1-1) and/or (S1-2)

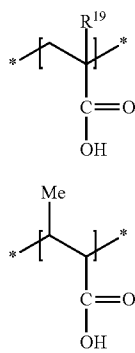

(S1-1)

(S1-2)

in which R$^{19}$ denotes a hydrogen atom or a methyl group and additionally at least one structural unit of formula (S) that is selected from at least one structural unit of formulas (S2-1) to (S2-8)

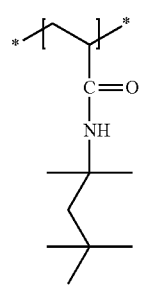

(S2-1)

(S2-2)

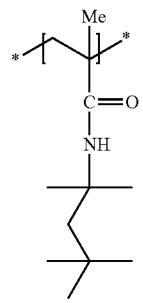

(S2-3)

(S2-4)

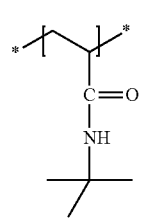

(S2-5)

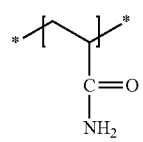

(S2-6)

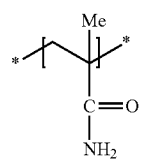

(S2-7)

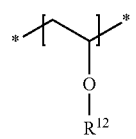

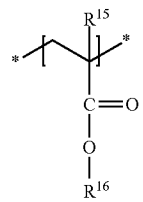

in which
R$^{12}$ denotes a (C$_2$ to C$_{12}$) acyl group (in particular acetyl or neodecanoyl), R$^{15}$ denotes a hydrogen atom or a methyl group, and R$^{16}$ denotes a (C$_1$ to C$_4$) alkyl group or a (C$_2$ to C$_4$) hydroxyalkyl group (in particular 2-hydroxyethyl). In the formulas above and all formulas to follow, a chemical bond identified by the symbol * denotes a free valence of the corresponding structural fragment.

In an exemplary embodiment, agents contemplated herein contain as an anionic setting polymer at least one polymer that contains at least one structural unit of formula (S1-2) and at least one structural unit of formula (S2-6)

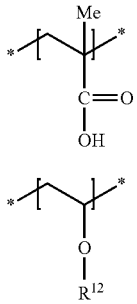

(S1-2)

(S2-6)

in which $R^{12}$ denotes a ($C_2$ to $C_{12}$) acyl group (in particular acetyl and/or neodecanoyl). Particularly preferred polymers of this kind are selected from at least one polymer of the group that is constituted from
copolymers of vinyl acetate and crotonic acid,
copolymers of vinyl propionate and crotonic acid,
copolymers of vinyl neodecanoate, vinyl acetate, and crotonic acid.

Such copolymers are made available, for example, by Clariant International of Switzerland under the commercial name Aristoflex A 60 (INCI name: VA/Crotonates Copolymer) in an isopropanol/water mixture (60 wt % active substance), by BASF SE of Germany under the commercial name Luviset CA 66 (vinyl acetate/crotonic acid copolymer 90:10, INCI name: VA/Crotonates Copolymer), and by National Starch of Bridgewater, N.J. under the commercial name Resyn 28-2942 or Resyn 28-2930 (INCI name: VA/Crotonates/Vinyl Neodecanoate Copolymer).

In a preferred embodiment, those compositions that contain as an anionic setting polymer at least one polymer that comprises at least one structural unit of formula (S1-1) and at least one structural unit of formula (S2-7)

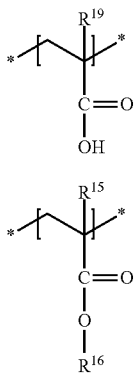

(S1-1)

(S2-7)

in which
$R^{15}$ and $R^{19}$ mutually independently denote a hydrogen atom or a methyl group,
$R^{16}$ denotes a ($C_1$ to $C_4$) alkyl group (in particular a methyl group or an ethyl group) or a ($C_2$ to $C_4$) hydroxyalkyl group (in particular 2-hydroxyethyl), are considered preferably suitable.

These polymers create a shape retention that is particularly compatible with the combination of ingredients (i) and (ii) of the agent contemplated herein. A hairstyle holds its shape extremely well and has a natural shine.

It is furthermore very particularly preferred in turn if the anionic setting polymer additionally contains, besides the above structural units of formulas (S1-1) and (S2-7), at least one structural unit of formula (S2-3)

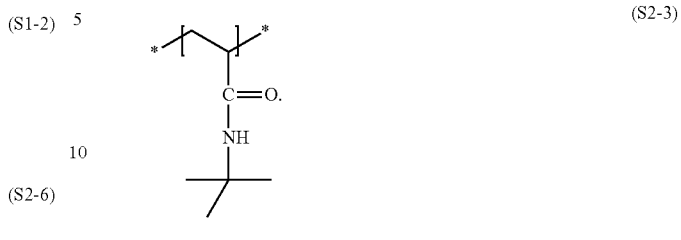

(S2-3)

It is preferred in turn if $R^{19}$ according to formula (S1-1) denotes a methyl group. Polymers of this type proven to be suitable are selected from at least one polymer of the group that is constituted from copolymers of acrylic acid and ethyl acrylate and N-tert-butylacrylamide. Such copolymers are furnished, for example, by BASF SE under the commercial name Ultrahold® Strong (INCI name: Acrylates/t-Butylacrylamide Copolymer; a white, pourable granulate) or Ultrahold® 8 (INCI name: Acrylates/t-Butylacrylamide Copolymer, a white, pourable granulate).

An agent of a particularly preferred embodiment contains as an anionic setting polymer at least one polymer that contains at least one structural unit of formula (S1-1) and at least one structural unit of formula (S2-7a) and at least one structural unit of formula (S2-7b)

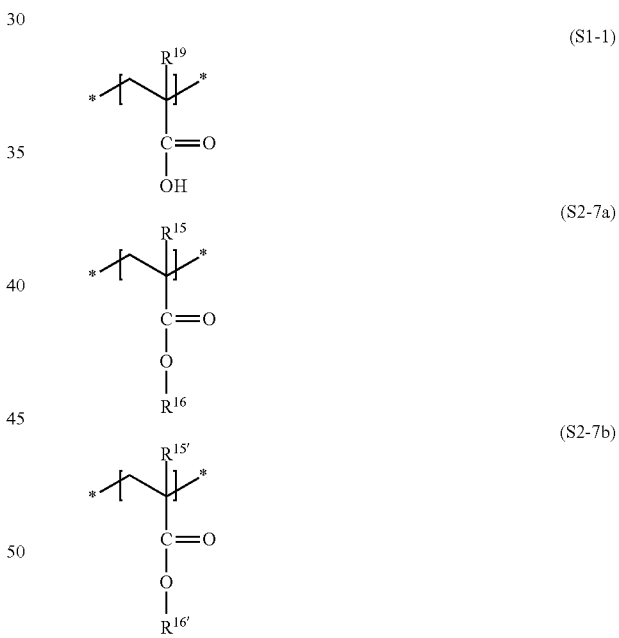

(S1-1)

(S2-7a)

(S2-7b)

in which
$R^{15}$, $R^{15'}$, and $R^{19}$ mutually independently denote a hydrogen atom or a methyl group,
$R^{16}$ denotes a ($C_1$ to $C_4$) alkyl group (in particular a methyl group and/or an ethyl group and/or a butyl group),
$R^{16'}$ denotes a ($C_2$ to $C_4$) hydroxyalkyl group (in particular 2-hydroxyethyl).

It is preferred if $R^{19}$ in formula (S1-1) denotes a methyl group.

It is preferred if $R^{15'}$ in formula (S2-7b) denotes a methyl group and $R^{16'}$ denotes a 2-hydroxyethyl group.

Copolymers that are produced by copolymerization of butyl acrylate, methyl methacrylate, ethyl acrylate, methacrylic acid, and 2-hydroxyethyl methacrylate are particularly preferred. Polymers having the INCI name Acrylates/Hydroxy Alkyl Esters Acrylates Copolymer are in turn very particularly preferred. One such polymer is obtainable, for example, from Dow Chemical Company of Midland, Mich. under the commercial name Acudyne® 1000.

An "amphoteric polymer" as used herein is a polymer that, in a protic solvent under standard conditions, carries structural units having anionic groups that must be compensated for by counter ions to maintain electroneutrality, and additionally comprises structural units having groups cationizable by protonation but is free of permanently cationized groups. "Anionic" groups include carboxyl groups and sulfonic-acid groups. "Permanently cationized" nitrogen atoms are to be understood as those nitrogen atoms which carry a positive charge and thereby form a quaternary ammonium compound. By definition, N-oxide-containing polymers are also included among the amphoteric polymers.

It is suitable if the additional amphoteric setting polymer contains at least one structural unit of formula (S1) that is selected from at least one structural unit of formulas (S1-1) to (S1-3).

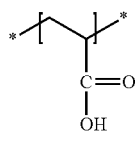
(S1-1)

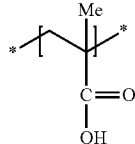
(S1-2)

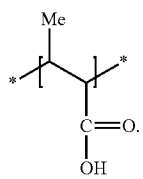
(S1-3)

and besides at least one structural unit of formulas (S1-1) to (S1-3) additionally contains at least one structural unit of formula (S2) that is selected from at least one structural unit of formulas (S2-9) to (S2-15)

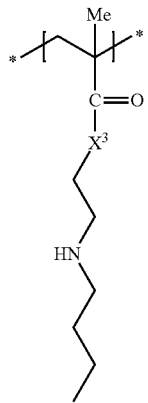
(S2-9)

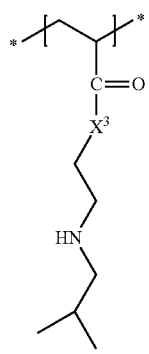
(S2-10)

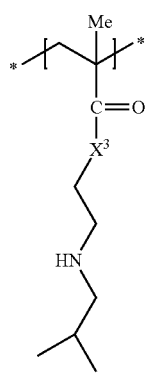
(S2-11)

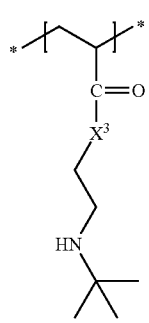
(S2-12)

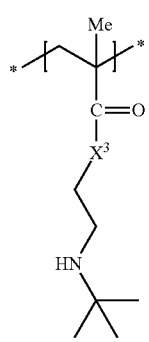
(S2-13)

(S2-14)

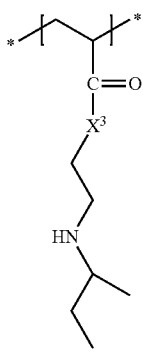

(S2-15)

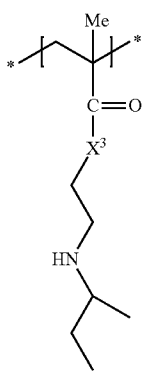

in which
X³ denotes an oxygen atom or an NH group.

It is in turn suitable if the amphoteric setting polymer additionally comprises, besides at least one structural unit of formulas (S1-1) to (S1-3) and at least one structural unit of formulas (S2-9) to (S2-15), at least one structural unit of formulas (S2-1) to (S2-8).

(S2-1)

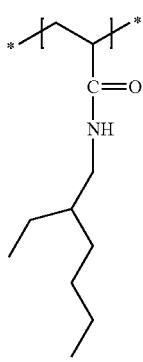

(S2-2)

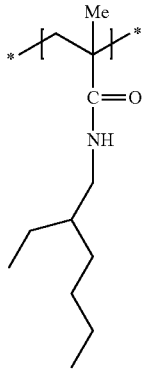

(S2-3)

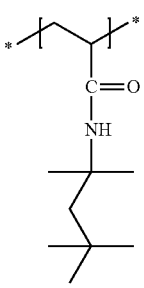

(S2-4)

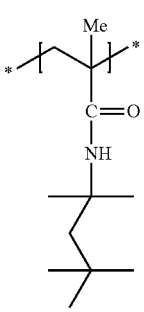

(S2-5)

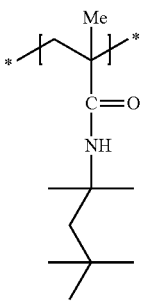

(S2-6)

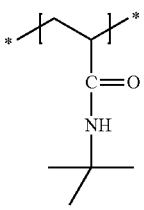

(S2-7)

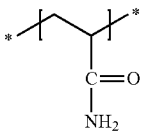

(S2-8)

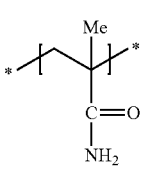

in which
$R^{12}$ denotes a ($C_2$ to $C_{12}$) acyl group (in particular acetyl or neodecanoyl).

An amphoteric setting polymer that contains at least one structural unit of formula (S1-1), at least one structural unit of formula (S2-3), and at least one structural unit of formula (S2-16) (selected in particular from the group that is constituted from the above formulas (S2-5) to (S2-12) with the provision that X³ denotes an oxygen atom)

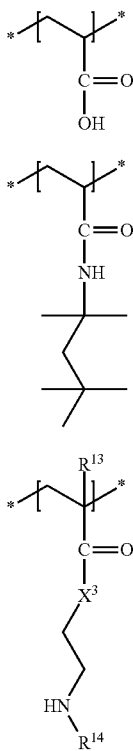

(S1-1)

(S2-3)

(S2-16)

in which X³ denotes an oxygen atom or an NH group,
R¹³ denotes a hydrogen atom or a methyl group, and
R¹⁴ denotes an alkyl group having 4 carbon atoms (in particular n-butyl, sec-butyl, isobutyl, or tert-butyl),
is preferably suitable.

It is particularly suitable in turn if the additional amphoteric setting polymer additionally contains, besides the above structural units of formulas (S1-1), (S2-3), and (S2-16), at least one structural unit of formula (S3)

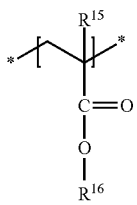

(S3)

in which
R¹⁵ denotes a hydrogen atom or a methyl group,
R¹⁶ denotes a (C₁ to C₄) alkyl group (in particular a methyl group or an ethyl group).

Additional amphoteric polymers of this kind are selected from the group that is constituted from copolymers of acrylic acid, (C₁ to C₄) alkyl acrylate, N—(C₄ alkyl)aminoethyl methacrylate, and N—(C₈ alkyl)acrylamide. An example of an amphoteric setting polymer usable in the context of this embodiment is the polymer obtainable under the commercial name Amphomer® from National Starch having the NCI name Octylacrylamide/Acrylates/Butylaminoethyl Methacrylate Copolymer.

A further additional amphoteric setting polymer comprises at least one monomer A1 selected from acrylic acid, methacrylic acid, acrylic acid alkyl esters, and methacrylic acid alkyl esters, and
at least one amphoteric monomer A2 of formula A2

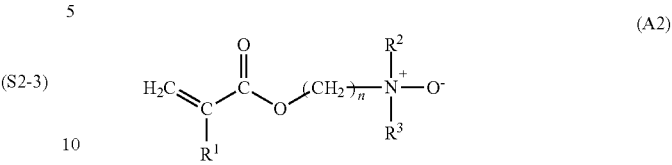

(A2)

wherein
R¹ denotes H or CH₃,
R² and R³ mutually independently each denote optionally branched C₁₋₁₀ alkyl, and
n denotes an integer from 1 to 20.

For purposes herein, what are to be understood as "additional amphoteric setting polymers" constituted from the aforesaid monomers are only those copolymers which contain, in addition to polymer units that result from incorporation of the aforesaid monomers A1 and A2 into the copolymer, a maximum of about 5 wt %, preferably a maximum of about 1 wt % of polymer units that are attributable to the incorporation of other monomers. Copolymers A preferably are constructed exclusively from polymer units that result from incorporation of the aforesaid monomers A1 and A2 into the copolymer.

Suitable monomers A1 are acrylic acid, methacrylic acid, acrylic acid C₁₋₂₀ alkyl esters, and methacrylic acid C₁₋₂₀ alkyl esters. Particularly suitably, monomer A1 is selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, methacrylic acid isopropyl ester, acrylic acid lauryl ester, methacrylic acid lauryl ester, acrylic acid cetyl ester, methacrylic acid cetyl ester, acrylic acid stearyl ester, and methacrylic acid stearyl ester, very particularly preferably from acrylic acid, methacrylic acid, acrylic acid methyl ester, methacrylic acid methyl ester, acrylic acid ethyl ester, methacrylic acid ethyl ester, acrylic acid lauryl ester, methacrylic acid lauryl ester, acrylic acid stearyl ester, and methacrylic acid stearyl ester.

Suitable monomers A2 are (meth)acryloylalkylamine oxides of formula A2, wherein R² and R³ denote, mutually independently in each case, methyl, ethyl, propyl, isopropyl, butyl, isobutyl, or tert-butyl, particularly preferably methyl. Suitable monomers A2 are furthermore chosen from the group comprising (meth)acryloylalkylamine oxides of formula A2 wherein n respectively denotes an integer from 1 to 5, preferably an integer from 1 to 3, and particularly preferably denotes 2.

Monomers A2 are preferably also selected from at least one monomer from the group including (meth)acryloylalkylamine oxides of formula A2 wherein R¹ respectively denotes CH₃.

Particularly suitably, monomers A2 are selected from at least one monomer from the group that is constituted from (meth)acryloylalkylamine oxides of formula A2 wherein R² and R³ mutually independently denote in each case methyl, ethyl, propyl, isopropyl, butyl, isobutyl, or tert-butyl, particularly preferably methyl, n denotes in each case an integer from 1 to 5, preferably an integer from 1 to 3 and particularly preferably 2, and R¹ respectively denotes CH₃. Very particularly suitably, monomer A2 is selected from at least one monomer from the group that is constituted from (meth)

acryloylalkylamine oxides of formula A2 wherein $R^1$, $R^2$, and $R^3$ respectively denote $CH_3$ and n denotes 2.

In a particularly suitable embodiment the agent contains at least one amphoteric setting polymer that is constituted from
at least two monomers A1, wherein the first monomer is selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, and methacrylic acid isopropyl ester, and the second monomer is selected from acrylic acid stearyl ester and methacrylic acid stearyl ester, and methacryloylethylamine oxide as monomer A2, in particular methacryloylethyl-N,N-dimethylamine oxide (in formula (A2): $R^1$=$CH_3$, n=2, $R^2$ and $R^3$=$CH_3$).

These copolymers, too, are known and are obtainable, for example, under the name Diaformer Z-632 from Clariant, the use of Diaformer Z-632 being particularly preferred.

In a suitable embodiment, the agent contemplated herein contains at least one amphoteric setting polymer that is constituted from
at least three monomers A1, wherein the first monomer is selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, and methacrylic acid isopropyl ester, the second monomer is selected from acrylic acid lauryl ester and methacrylic acid lauryl ester, and the third monomer is selected from acrylic acid stearyl ester and methacrylic acid stearyl ester and
methacryloylethylamine oxide as monomer A2, in particular methacryloylethyl-N,N-dimethylamine oxide (in formula (A2): $R^1$=$CH_3$, n=2, $R^2$ and $R^3$=$CH_3$).

Corresponding copolymers are likewise known and are obtainable e.g. under the designations Diaformer Z-611, Diaformer Z-612, Diaformer Z-613, Diaformer Z-631, Diaformer Z-633, Diaformer Z-651, Diaformer Z-711N, Diaformer Z-712N, and Diaformer Z-731N from the Clariant company; the use of Diaformer Z-712N and Diaformer Z-651 is preferred.

In a further preferred embodiment the agent contemplated herein contains, in addition to the anionic setting polymer, at least one nonionic setting polymer.

A "nonionic polymer" as used herein is a polymer that, in a protic solvent under standard conditions, carries substantially no structural units having permanently cationic or anionic groups that must be compensated for by counter ions to maintain electroneutrality. "Cationic groups" encompass, for example, quaternized ammonium groups but not protonated amines. "Anionic groups" encompass, for example, carboxyl groups and sulfonic-acid groups.

The additional nonionic setting polymers are favorably selected from at least one polymer of the group that is constituted from
homopolymers and nonionic copolymers of N-vinylpyrrolidone,
nonionic copolymers of isobutene,
nonionic copolymers of maleic acid anhydride. Agents contemplated herein that contain, as an additional nonionic setting polymer, at least one polymer selected from the group that is constituted from
polyvinylpyrrolidone,
copolymers of N-vinylpyrrolidone and vinyl esters of carboxylic acids having 2 to 18 carbon atoms, in particular of N-vinylpyrrolidone and vinyl acetate,
copolymers of N-vinylpyrrolidone and N-vinylimidazole and methacrylamide,
copolymers of N-vinylpyrrolidone and N-vinylimidazole and acrylamide,
copolymers of N-vinylpyrrolidone with N,N-di-($C_1$ to $C_4$) alkylamino-($C_2$ to $C_4$) alkylacrylamide,
or mixtures of these polymers, are particularly preferred. Agents that contain, as an additional nonionic polymer, at least one polymer selected from the group that is constituted from
polyvinylpyrrolidone,
copolymers of N-vinylpyrrolidone and vinyl esters of carboxylic acids having 2 to 18 carbon atoms, in particular of N-vinylpyrrolidone and vinyl acetate, or mixtures of these polymers, are very particularly preferred.

Suitable polyvinylpyrrolidones are, for example, commercial products such as Luviskol® K 90 or Luviskol® K 85 of the BASF SE company. When copolymers of N-vinylpyrrolidone and vinyl acetate are used, it is in turn suitable if the molar ratio of the contained structural units of the polymer from the N-vinylpyrrolidone monomer to the contained structural units of the polymer from the vinyl acetate monomer is in the range from 20:80 to 80:20, in particular from 30:70 to 60:40.

Suitable copolymers of vinylpyrrolidone and vinyl acetate are obtainable, for example, from the BASF SE company under the trademarks Luviskol® VA 37, Luviskol® VA 55, Luviskol® VA 64, and Luviskol® VA 73.

Also suitable are those agents that contain at least one nonionic setting polymer comprising at least one structural unit of formula (M-I) and at least one structural unit of formula (M-IV)

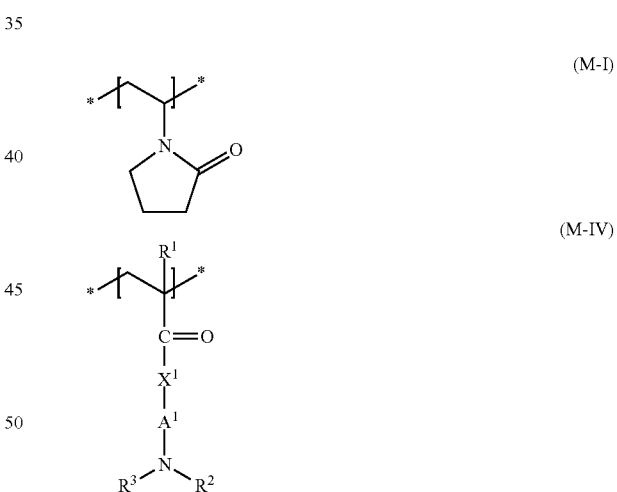

in which
$R^1$ denotes a hydrogen atom or a methyl group,
$X^1$ denotes an oxygen atom or an NH group,
$A^1$ denotes an ethane-1,2-diyl, propane-1,3-diyl, or butane-1,4-diyl group,
$R^2$ and $R^3$ mutually independently denote a ($C_1$ to $C_4$) alkyl group. It is particularly favorable if the above nonionic setting polymer is selected from at least one polymer that, for formula (M-IV), conforms to at least one or more of the following features:
$R^1$ signifies a methyl group,
$X^1$ denotes an NH group,
$A^1$ denotes ethane-1,2-diyl or propane-1,3-diyl, $R^2$ and $R^3$ mutually independently denote methyl or ethyl (particularly preferably methyl).

The group of the polymers vinylcaprolactam/vinylpyrrolidone/dimethylaminoethyl methacrylate copolymer (for example, INCI name: Vinyl Caprolactam/PVP/Dimethylaminoethyl Methacrylate Copolymer, under the trade name Gaffix® VC 713 (ISP)), vinylpyrrolidone/vinylcaprolactam/dimethylaminopropyl methacrylamide copolymer (e.g. INCI name: VP/Vinyl Caprolactam/DMAPA Acrylates Copolymer, under the trade name Aquaflex® SF 40 (ISP)), vinylcaprolactam/vinylpyrrolidone/dimethylaminoethyl methacrylate copolymer (for example, as 35 to 39% solids in ethanol in the form of the commercial product Advantage LC E having the INCI name: Vinyl Caprolactam/VP/Dimethylaminoethyl Methacrylate Copolymer, Alcohol, Laurylpyrrolidone (ISP)), vinylpyrrolidone/dimethylaminopropylmethacrylamide copolymer (for example, INCI name: VP/DMAPA Acrylates Copolymer, under the trade name Styleze CC-10 (10 wt % active substance) (ISP)), is in turn considered a list for selection therefrom of at least one or more additional nonionic setting polymers.

The agents contemplated herein can furthermore contain adjuvants and additives.

The agent can additionally contain as a care-providing substance, for example, at least one protein hydrolysate and/or a derivative thereof. Protein hydrolysates of vegetable origin, for example soy, almond, pea, moringa, potato, and wheat protein hydrolysates, are obtainable, for example, under the trademarks Gluadin® (Cognis), DiaMin® (Diamalt), Lexein® (Inolex), Hydrosoy® (Croda), Hydrolupin® (Croda), Hydrosesame® (Croda), Hydrotritium® (Croda), and Crotein® (Croda). Protein hydrolysates can be contained in the agents, for example, in concentrations from about 0.01 wt % to about 20 wt %, preferably from about 0.05 wt % to about 15 wt %, and very particularly preferably in quantities from about 0.05 wt % to about 5 wt %, based in each case on the total utilization preparation.

The agents contemplated herein can furthermore additionally contain at least one vitamin, provitamin, vitamin precursor, and/or derivative thereof. Those vitamins, provitamins, and vitamin precursors which are usually assigned to the groups A, B, C, E, F, and H are preferred. Panthenol, pantolactone, pyridoxine and derivatives thereof, as well as nicotinic acid amide and biotin, are particularly preferred. In a preferred embodiment the agents contain panthenol, preferably in a quantity from about 0.1 to about 5 wt % based in each case on the total agent.

In an embodiment, the agents furthermore additionally contain at least one plant extract. The extracts from green tea, oak bark, nettle, witch hazel, hops, henna, chamomile, burdock root, horsetail, hawthorn, linden blossoms, almond, aloe vera, pine needles, horse chestnut, sandalwood, juniper, coconut, mango, apricot, lemon, wheat, kiwi fruit, melon, orange, grapefruit, salvia, rosemary, birch, mallow, lady's-smock, wild thyme, yarrow, thyme, lemon balm, restharrow, coltsfoot, hibiscus, meristem, ginseng, and ginger root are especially preferred.

Further active agents, adjuvants, and additives are, for example:

structuring agents such as maleic acid and lactic acid,
perfume oils, dimethyl isosorbide, and cyclodextrins,
defoaming agents such as silicones,
dyes for coloring the agent,
substances for adjusting pH, for example usual acids, in particular edible acids, and bases, consistency agents such as sugar esters, polyol esters, or polyolalkyl ethers, complexing agents such as EDTA, NTA, β-alaninediacetic acid, and phosphonic acids, swelling and penetration substances such as propylene glycol monoethyl ether, carbonates, hydrogen carbonates, guanidines, ureas, and primary, secondary, and tertiary phosphates,
preservatives,
antioxidants.

With regard to further optional components as well as the quantities of those components used, reference is made expressly to the relevant manuals known to one skilled in the art.

The agents contemplated herein can be formulated in all usual forms, for example in the form of solutions that can be applied onto the hair as a lotion or as a pump spray or aerosol spray, or other preparations that are suitable for use on the hair.

The agents are preferably configured as a pump spray or in particular as an aerosol spray.

For the embodiment as a pump spray, the agents are present in a non-aerosol container having a spraying apparatus. For the embodiment as an aerosol spray the agents additionally comprise at least one propellant, and are packaged in a pressurized-gas container ("aerosol container") having a spraying apparatus.

The pressurized-gas containers with which a product is distributed through a valve as a result of the internal gas pressure of the container are referred to by definition as "aerosol containers." A "non-aerosol container" is defined, conversely to the "aerosol" definition, as a vessel under standard pressure with which a product is distributed by means of mechanical action by way of a pump system. The agents are present particularly preferably, as described earlier, as a spray mist. For this purpose it is in turn preferred to configure the agents as an aerosol spray. Agents preferred (in particular the preferred embodiments (A) to (M), see above) therefore particularly preferably additionally contain at least one propellant. The preferred propellants and/or the preferred utilization quantities of the propellant are those of the second embodiment.

In accordance with a second embodiment, an aerosol spray contains a cosmetic agent of the first embodiment packaged in an aerosol container having a spraying apparatus, said cosmetic agent additionally comprising at least one propellant. Agents contemplated herein that are present in the form of an aerosol product can be manufactured in usual fashion. As a rule all the constituents of the agent are introduced into a suitable pressure-tight container. The latter is then sealed with a valve. Lastly, the desired quantity of propellant is introduced using conventional techniques.

In an embodiment as an aerosol spray, suitable propellants are selected, for example, from $N_2O$, dimethyl ether, $CO_2$, air, alkanes having 3 to 5 carbon atoms such as propane, n-butane, isobutane, n-pentane, and isopentane, and mixtures thereof. Dimethyl ether, propane, n-butane, isobutane, and mixtures thereof are preferred. In accordance with a preferred embodiment, the aforesaid alkanes, mixtures of the aforesaid alkanes, or mixtures of the aforesaid alkanes with dimethyl ether are used as the only propellant. Also contemplated are the concurrent use of propellants of the fluorochlorocarbon type, but in particular fluorocarbons.

The propellant is contained in the agents, in the embodiment as an aerosol spray, preferably in a quantity from about 30 to about 60 wt %, in particular from about 35 to about 55 wt %, based on the weight of the total agent.

Very particularly preferably, mixtures of propane and butane are used as the only propellant, at a weight ratio of propane to butane from about 70:30 to about 10:90. These mixtures are in turn used in the agents preferably in a quantity from about 30 to about 55 wt %, based on the weight of the total agent. "Butane" is understood herein as n-butane, isobutane, and mixtures of n-butane and isobutane.

In addition, the preferred embodiments of the cosmetic agents of the first embodiment, in particular the embodiments (A) to (M), are likewise considered mutatis mutandis in particular to be preferably suitable.

For a given spraying apparatus, the sizes of the aerosol droplets and the respective size distribution can be adjusted by way of the quantitative ratio of propellant to the other constituents of the preparations.

The spray rate of the sprays is preferably about 5.0 to about 15.0 g/10 s, particularly preferably about 6.0 to about 10.0 g/10 s. Use of the previously recited additionally preferred cosmetic agents of the first embodiment (see above) is of course also preferred in the context of the embodiment as an aerosol spray.

The agents contemplated herein, and products that contain said agents, in particular aerosol hair sprays, are notable in particular for the fact that they impart a very natural shine to treated hair. A second embodiment is the use of an agent of the first embodiment to produce shine on keratin-containing fibers, in particular human hair. It is preferred in this context to configure the agent of the first embodiment as a spray, in particular as an aerosol spray of the second embodiment.

A third embodiment is a method for treating keratin-containing fibers, in particular human hair, in which an agent contemplated herein is applied, in particular as a spray, onto the keratin-containing fibers.

It is further preferred if, after application of the agent, the agent remains on the keratin-containing fibers, i.e. is not rinsed out again. Also preferred are those methods in which a utilization of a dry shampoo containing at least one absorbent (in particular starch or derivatives thereof (such as preferably rice starch and/or starch octenyl succinate) and/or silica), and/or of a cosmetic agent containing at least one polymer having a setting effect, has directly preceded the application of the cosmetic agent contemplated herein. Suitable as preferably suitable polymers having a setting effect are, in particular, those recited in the context of the first embodiment (see above).

EXAMPLES

Unless otherwise noted, the quantity indications below are understood as percentages by weight.

The following formulas were furnished by mixing the indicated raw materials with the exception of the propellant, and introduced into an aerosol spray can. The aerosol cans were sealed with the valve, and lastly the corresponding propellant was added through the valve:

| Raw materials | A | B | C |
| --- | --- | --- | --- |
| Dimethicone | — | — | 2.50 |
| Octamethyltrisiloxane | 5.00 | 10.00 | 2.50 |
| Benzoic acid $C_{12}$-$C_{15}$ alkyl ester | 2.50 | 5.00 | 5.00 |
| Perfume | 0.10 | 0.10 | 0.10 |
| Propellant (mixture of 15% propane, 85% butane) | 50.00 | 50.00 | 50.00 |
| Ethanol, denatured | to 100 | to 100 | to 100 |

The effect of the agents A, B, and C contemplated herein on non-pretreated hair strands and on hair strands pretreated with a dry shampoo was tested. After spray application onto the non-pretreated hair, the agents produced a natural shine. The hair was loose, not weighted down, and was easy to comb. The same was observed when the hair had been pretreated with the following aerosol dry shampoo by spraying on, allowing 10 minutes of contact, and combing out:

| Raw material | wt % |
| --- | --- |
| Rice starch | 5.00 |
| Ethanol | 10.00 |
| Perfume | 0.10 |
| Butane | to 100 |

The invention claimed is:

1. An aerosol spray in an aerosol container having a spraying apparatus, the aerosol spray comprising:
    a cosmetic agent comprising in a cosmetically acceptable carrier:
    at least one ester of formula (I)

in which
        $R^1$ signifies a linear or branched ($C_2$ to $C_{30}$) alkyl group, a linear or branched ($C_8$ to $C_{30}$) alkenyl group, a ($C_2$ to $C_{30}$) alkylpoly(oxyethylene) group, an optionally substituted aryl group, an optionally substituted aryl-($C_1$ to $C_4$) alkyl group, or a ($C_2$ to $C_6$) hydroxyalkyl group, and
        $R^2$ signifies an optionally substituted aryl group, a linear or branched ($C_8$ to $C_{30}$) alkyl group, a linear or branched ($C_8$ to $C_{30}$) alkenyl group, an optionally substituted aryl-($C_1$ to $C_4$) alkyl group, an optionally substituted aryl-($C_2$ to $C_4$) alkenyl group, or a ($C_2$ to $C_6$) hydroxyalkyl group,
    an alcohol that comprises 2 to 6 carbon atoms and 1 to 3 hydroxyl groups,
    octamethyltrisiloxane, and
    a propellant.

2. A method of imparting shine on keratin-containing fibers, the method comprising the steps of:
    applying to the keratin-containing fibers a dry shampoo and/or a cosmetic agent containing at least one polymer having a setting effect; and
    subsequently applying to the keratin-containing fibers an agent comprising in a cosmetically acceptable carrier:
    at least one ester of formula (I)

in which
        $R^1$ signifies a linear or branched ($C_2$ to $C_{30}$) alkyl group, a linear or branched ($C_8$ to $C_{30}$) alkenyl group, a ($C_2$ to $C_{30}$) alkylpoly(oxyethylene) group, an optionally substituted aryl group, an optionally substituted aryl-($C_1$ to $C_4$) alkyl group, or a ($C_2$ to $C_6$) hydroxyalkyl group, and R² signifies an optionally substituted aryl group, a linear or branched ($C_8$ to $C_{30}$) alkyl group, a linear or branched ($C_8$ to $C_{30}$) alkenyl group, an optionally substituted aryl-($C_1$ to $C_4$) alkyl group, an optionally substituted aryl-($C_2$ to $C_4$) alkenyl group, or a ($C_2$ to $C_6$) hydroxyalkyl group, an alcohol that comprises 2 to 6 carbon atoms and 1 to 3 hydroxyl groups, and octamethyltrisiloxane, and a propellant.

3. The aerosol spray according to claim 1, wherein the agent contains, as an ester of formula (I), at least one ester of formula (I-a)

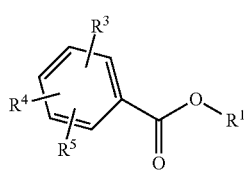

(I-a)

in which

R¹ denotes a linear or branched ($C_3$ to $C_{24}$) alkyl group, a linear or branched ($C_6$ to $C_{24}$) alkenyl group, an optionally substituted aryl group, an optionally substituted aryl-($C_1$ to $C_4$) alkyl group, or a ($C_2$ to $C_6$) hydroxyalkyl group, and R³, R⁴, and R⁵ mutually independently denote a hydrogen atom, hydroxy, amino, ($C_1$ to $C_4$) alkylamino, di-($C_1$ to $C_4$) alkylamino, ($C_1$ to $C_4$) alkyl, ($C_1$ to $C_4$) alkoxy, ($C_1$ to $C_4$) alkoxycarbonyl, or two of the residues form, together with the remainder of the molecule, a five- or six-membered ring.

4. The aerosol spray according to claim 1, wherein R¹ denotes a linear or branched ($C_4$ to $C_{18}$) alkyl group, a linear or branched ($C_8$ to $C_{22}$) alkenyl group, an optionally substituted aryl group, an optionally substituted aryl-($C_1$ to $C_4$) alkyl group, or a ($C_2$ to $C_6$) hydroxyalkyl group.

5. The aerosol spray according to claim 1, wherein said ester is present, based on the total weight of the agent, in a quantity from about 0.5 to about 15.0 wt %.

6. The aerosol spray according to claim 1, wherein said ester, based on the total weight of the agent, is present in a quantity from about 1.0 to about 10.0 wt %.

7. The aerosol spray according to claim 1, wherein the agent further comprises as a component (iii) an additional silicone oil of formula (Si-1)

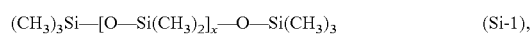

in which x denotes a number from 2 to 100.

8. The aerosol spray according to claim 1, wherein said additional silicone oil of component (iii) is present, based on the total weight of the agent, in a quantity from about 0.5 to about 20.0 wt %.

9. The aerosol spray according to claim 1, wherein said octamethyltrisiloxane of component (ii) is present, based on the total weight of the agent, in a quantity from about 0.5 to about 20.0 wt %.

10. The aerosol spray according to claim 9, wherein said octamethyltrisiloxane of component (ii) is present, based on the total weight of the agent, in a quantity from about 1.0 to about 15.0 wt %.

11. The aerosol spray according to claim 1, wherein the alcohol having at least 2 to 6 carbon atoms is present in a quantity, based on the weight of the agent, from about 30.0 to about 70.0 wt %.

* * * * *